US006436126B1

(12) United States Patent
McAfee

(10) Patent No.: US 6,436,126 B1
(45) Date of Patent: Aug. 20, 2002

(54) HEAD FLEXION MECHANISM FOR CHIROPRACTIC TABLE

(75) Inventor: Brent McAfee, Lisbon, IA (US)

(73) Assignee: Lloyd Table Company, Lisbon, IA (US)

(*) Notice: Subject to any disclaimer, the term of this patent is extended or adjusted under 35 U.S.C. 154(b) by 0 days.

(21) Appl. No.: 09/681,153

(22) Filed: Jan. 31, 2001

(51) Int. Cl.⁷ .................................................. A61F 5/00
(52) U.S. Cl. ........................ 606/245; 606/242; 128/845
(58) Field of Search ................................ 606/237, 240, 606/241–245; 128/845; 601/86, 90–92, 98, 101, 115; 5/622

(56) References Cited

U.S. PATENT DOCUMENTS

| | | | | | |
|---|---|---|---|---|---|
| 4,649,905 | A | * | 3/1987 | Barnes | 606/245 |
| 4,660,549 | A | * | 4/1987 | Kowalski et al. | 606/242 |
| 4,724,828 | A | | 2/1988 | Barnes et al. | |
| 4,732,141 | A | | 3/1988 | Steffensmeier | |
| 5,192,306 | A | | 3/1993 | Scott et al. | |
| 5,423,861 | A | * | 6/1995 | Kelley | 606/241 |
| 5,922,011 | A | * | 7/1999 | Cuccia | 606/241 |

* cited by examiner

*Primary Examiner*—Danton D. DeMille
*Assistant Examiner*—Quang D Thanh
(74) *Attorney, Agent, or Firm*—James C. Nemmers

(57) ABSTRACT

A mounting for the head section of a chiropractic table that allows the practitioner to maintain a much greater degree of control over the various manipulations typically performed on the patient. The head support section has a cushion that is mounted for slideable movement along the longitudinal axis of the table which coincides with the patient's spine. A linkage arrangement allows the proximal end of the cushion to remain substantially the same distance from the chest lumbar section of the table as the head section is tilted downwardly. This allow a controlled flexion movement of the patient's cervical spine. The amount of gap and thus the amount of flexion can be adjusted by adjusting the linkage that is a part of the head section structure. In addition, the slideable movement of the head cushion longitudinally allows the practitioner to apply traction to the patient's spine with or without flexion, if such a movement is determined to be desirable.

5 Claims, 3 Drawing Sheets

HEAD FLEXION MECHANISM FOR CHIROPRACTIC TABLE

BACKGROUND OF INVENTION

There are known and commercially available to practicing chiropractors and other health practitioners numerous types of tables to assist them in conducting examinations, adjustments and treatments beneficial to a patient. When such tables are used for chiropractic adjustments, the tables are commonly designed so that the patient support is separated into separate sections for the head, chest, lumbar, pelvic and foot sections. Typically, each of these sections is independently supported on a frame, and some of the sections are moveable in ways that permit the health practitioner to conduct the desired adjustment or treatment. For example, some of the sections are constructed with a mechanism that allows the section to be displaced a predetermined distance or pivoted a predetermined amount to facilitate a particular adjustment performed by the health practitioner.

The head section of chiropractic tables is typically designed and mounted so that it can produce one or more motions. For example, some head sections are mounted so that they can pivot as a unit in a curved path about an axis extending longitudinally along the patient's spine so that the health practitioner can impart a twisting motion on the patient's head and thus make a rotation adjustment. In addition, the head section is typically mounted on a vertical pivot at its proximal end so that the distal end can be swung from side to side which permits the health practitioner to perform a lateral flexion of the patient's head. Other tables are also pivotally mounted at the proximal end for movement about a horizontal axis so that the distal end at the top of the patient's head can be tilted upwardly and downwardly to provide a flexion adjustment. In addition, some tables provide for movement of the patient's head linearly along the spine to stretch a cervical portion of the spine and thereby induce traction on the patient's cervical spine.

In those tables where the head section is mounted for pivotal movement about a horizontal axis so that the distal end can be tilted upwardly and downwardly to produce flexion of the patient's cervical spine, the distance between the proximal end of the head section cushion and the adjoining chest-lumbar section will increase as the distal end of the head section tilts downwardly. Since the patient's trunk does not move, this gap can produce excessive flexion on the patient's spine and more flexion than the health practitioner wishes to produce. It can also produce traction even when the practitioner does not wish to induce traction on the spine.

Tables that are known in the prior art thus deprive the chiropractor or other practitioner with a lack of control over the amount of flexion that the practitioner has determined is desirable to treat the patient's condition. Also, the known designs of chiropractic tables provide only for the pivotal movement of flexion, and if the practitioner wishes to also apply traction to the patient, the practitioner must grasp the patient's head and lift it from the head section and apply traction directly. The head sections of known chiropractic tables do not provide for movement of the head section to allow both traction and flexion to occur using the same table.

Therefore there is a need for an improved chiropractic table which has a head section that allows the practitioner to perform a variety of manipulations more easily and more controlled than allowed on known chiropractic tables.

SUMMARY OF INVENTION

The invention provides a mounting for the head section of a chiropractic table that allows the practitioner to maintain a much greater degree of control over the various manipulations typically performed on the patient. The head support section therefore has a cushion that is mounted for slideable movement along the longitudinal axis of the table which coincides with the patient's spine. With the linkage arrangement described in detail hereinafter, the proximal end of the cushion will maintain a close position to the chest lumbar section of the table as the head section is tilted downwardly to allow a controlled flexion movement of the patient's cervical spine. This can be done either with or without applying traction to the patient's spine. The amount of gap and thus the amount of flexion can be adjusted by adjusting the linkage that is a part of the head section structure. In addition, the slideable movement of the head cushion longitudinally allows the practitioner to apply traction to the patient's spine with or without flexion, if such a movement is determined to be desirable.

DETAILED DESCRIPTION

Figure 1:
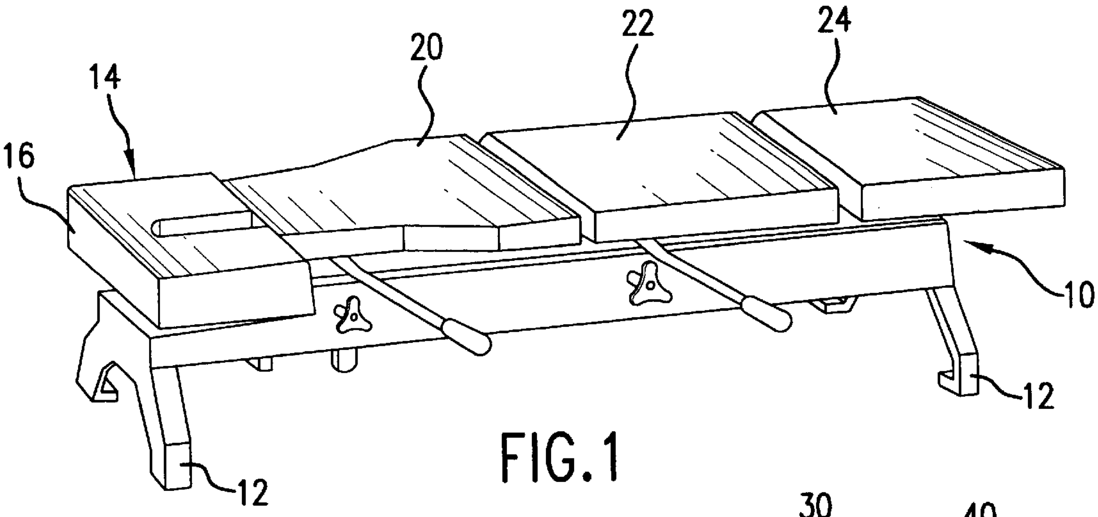
FIG. 1 is a perspective view of a chiropractic table having multiple, independent sections.
Figure 2:
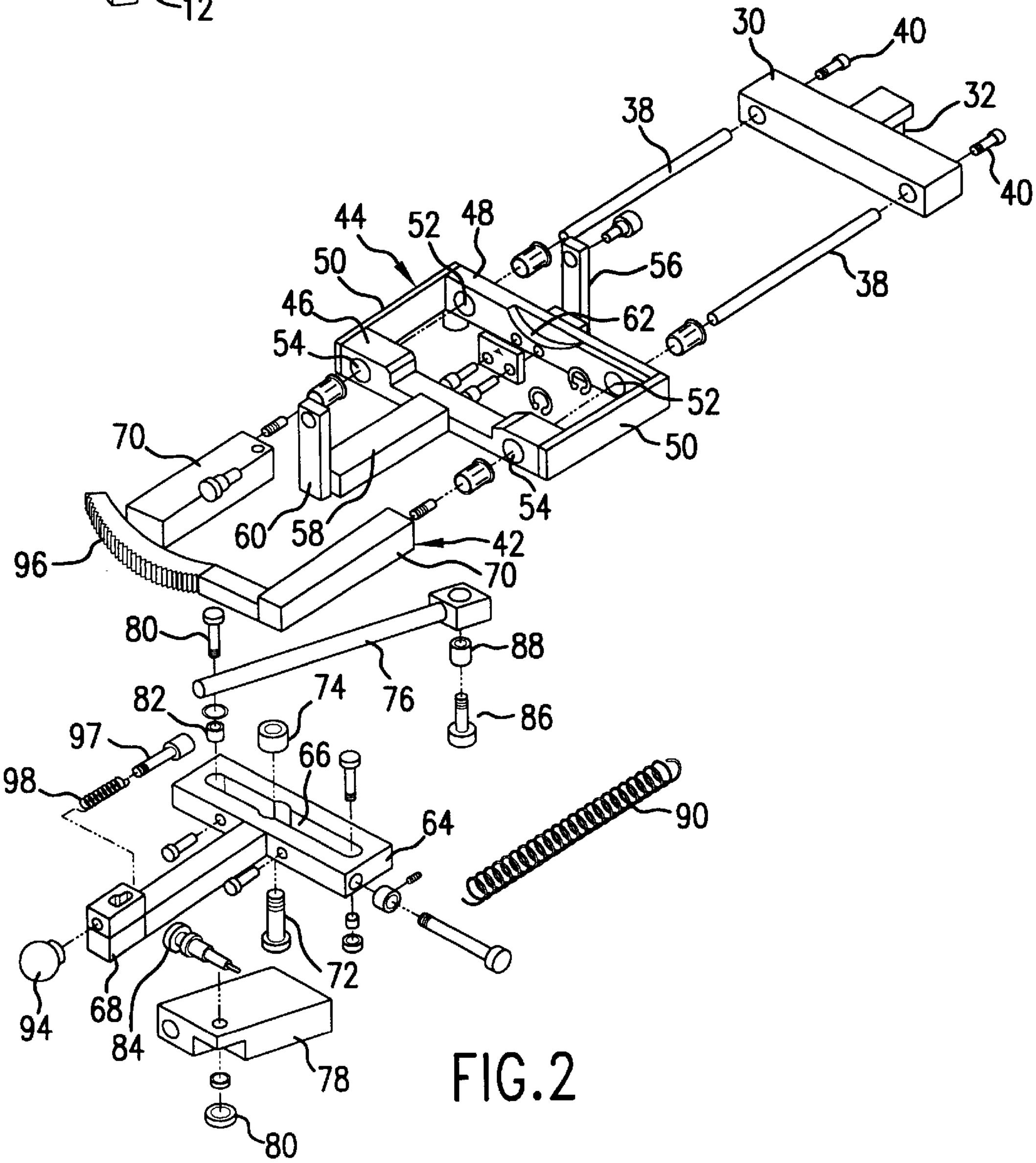
FIG. 2 is an exploded perspective view of the mounting structure for the head section of the table.
Figure 3:
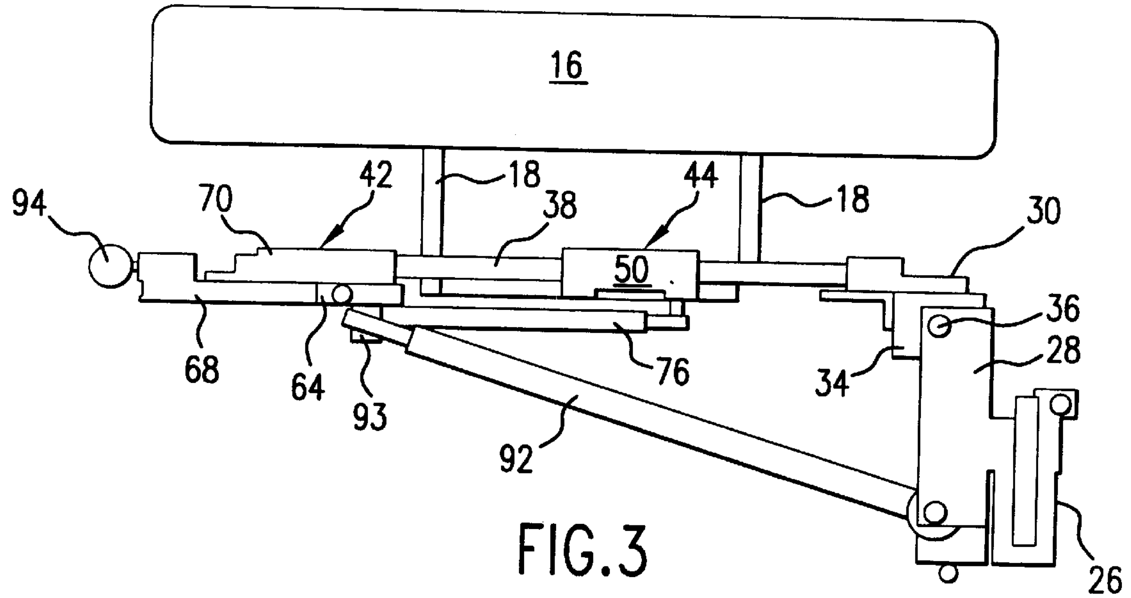
FIG. 3 is a side elevational view of the head section.

The invention relates to and is employed in connection with a patient support such as a table which is used for the examination or treatment of the patient. The preferred embodiment is described in connection with a chiropractic table that has separate and typically independently moveable patient support sections. Referring to FIG. 1 of the drawings, there is illustrated a chiropractic table which has a table frame 10 supported by legs 12. At the head of a table is a head section indicated generally by the reference numeral 14 which has a cushion 16 mounted on supports 18 (FIG. 3). The head section 14 is mounted on the table frame 10 in the manner described hereinafter. The table also includes a chest-lumbar section 20, a pelvic section 22, and a foot section 24. As is well known to those skilled in the art, each of the sections 20, 22 and 24 are secured to the table frame 10 in any suitable manner depending upon the particular table and the purposes for which it is specifically designed.

Figure 4:
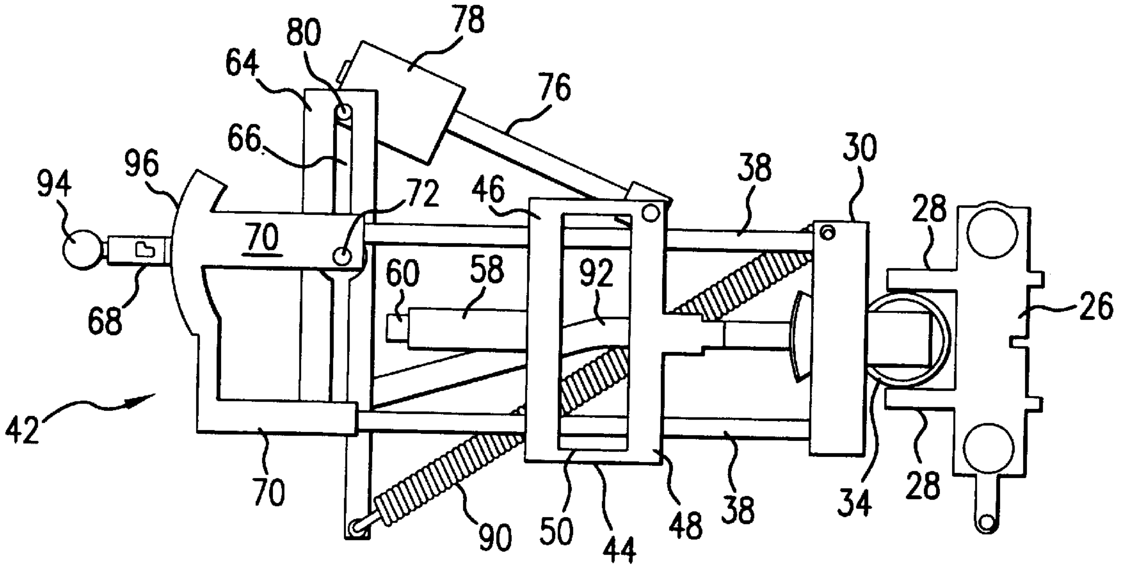
FIG. 4 is a top or plan view of the head section with the cushion removed.
Figure 5:
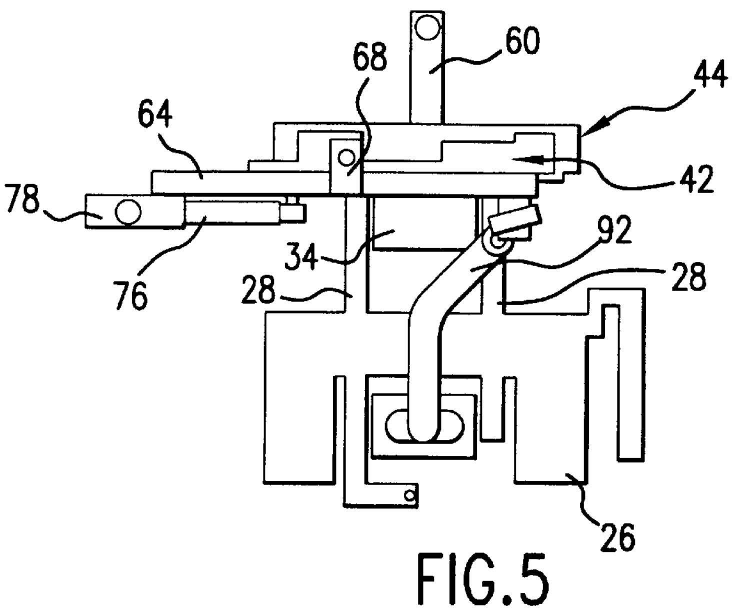
FIG. 5 is an end view of the head section.

Referring now to FIGS. 2, 3, 4 and 5, the head section 14 is shown in detail. As best seen in FIGS. 3, 4 and 5, the table frame 10 includes a horizontal support bar 26 with two forwardly extending support arms 28 to which is pivotally mounted a T-shaped support block 30. Block 30 has a downwardly extending pivot rod 32 (FIG. 2) that turns within a sleeve 34 therefore providing for swinging movement of the entire head section 14 from side to side if the practitioner desires to apply lateral flexion. The T-shaped support block 30 is also secured to the supports arms 28 for vertical pivoting movement about a pivot axle 36 that is secured to the support arms 28.

Secured to and extending forwardly from the T-shaped support block 30 are guide members such as a pair of laterally spaced apart guide rods 38. Rods 38 may be secured to the support block 30 by fasteners 40. The outer or distal ends of the guide rods 38 are secured to a lock frame assembly indicated generally by the reference numeral 42. Mounted on the guide rods 38 is a slide bracket assembly 44 which includes a front member 46 and a rear member 48 which is rigidly joined to the front member 46 by side members 50. Members 46, 48 and 50 form a rigid rectangular frame which has openings 52 extending through the rear member 48 and openings 54 extending through the front member 46. Openings 52 and 54 are in alignment to receive the guide rods 38, thus providing for slideable movement of the slide bracket assembly 44 back and forth along the guide rods 38.

Extending upwardly from the rear member 48 of the slide bracket assembly 44 is a vertical support 56. Similarly, an L-shaped vertical support 58 is affixed to the front member 46, and support member 58 has a leg 60 extending upwardly. The vertical support 56 and leg 60 provide a mounting for the cushion 16 and its supports 18. The particular manner of mounting the cushion 16 and supports 18 to the slide bracket assembly 44 is not shown in detail since it forms no part of the invention and is well known to those skilled in the art. However, typically the supports 18 would be mounted in a suitable manner on the vertical support 56 and the leg 60 so as to provide for a swinging motion of the cushion 16 in the event the practitioner wishes to apply rotation to the head of the patient. It will be understood by those skilled in the art that this rotation movement is applied by swinging the cushion 16 in a curved path about an arc that is represented by the concave surface 62 formed in the rear member 48 of the slide bracket assembly 44. Motion of this type is illustrated in U.S. Pat. No. 4,732,141 as applied to a chest-lumbar section.

The lock frame assembly 42 includes a rocker arm 64 that has a transverse slot 66 and a forwardly extending locking arm 68. The rocker arm 64 is pivotally attached to support arms 70 of frame assembly 42 by means of a suitable fastener 72 and roller bearing 74. A linkage bar 76 is slideably engaged with a lock block 78 which in turn is attached at a selected position in the slot 66 of the rocker arm 64 by a locking fastener 80 and bushing 82. The linkage bar 76 is locked inside of the lock block 78 by a lock bolt 84. The linkage bar 76 must be locked to the lock block 78 during tilting of the head section 14 to induce flexion to the patient. The proximal end of the linkage bar 76 is pivotally attached to the rear member 48 of the slide bracket assembly 44 by a suitable fastener 86 and bushing 88.

As best seen in FIGS. 3 and 4, a push rod 92 has its proximal end pivotally connected to the frame support bar 26 and the other end pivotally connected to the rocker arm 64 by fastener 93. As best seen in FIGS. 4 and 5, the push rod 92 is curved to produce the desired push-pull action on the rocker arm 64 as described hereinafter. To provide for return of the head section to its normal position, a return spring 90 has one end attached to the rocker arm 64 while the proximal end of the spring 90 has its other end attached in any suitable manner to the T-shaped support block 30.

As indicated above, the rocker arm 64 which forms a part of the lock frame assembly 42 is pivotally moveable about the roller bearing 74. To lock the rocker arm 64 in a selected position and thus prevent the head section 14 from tilting, a lock knob 94 at the outer end of the locking arm 68 controls the movement of a locking pin 97 that slide in the locking arm 68 into and out of engagement with the curved locking member 96. The curved surface of the locking member 96 is preferably formed from a ring gear to provide a positive lock with the locking pin 97, which pin 97 is biased into a locking position by spring 98. The locking member 96 also provides for locking the head section 14 at any desired degree of tilt.

Figure 7:
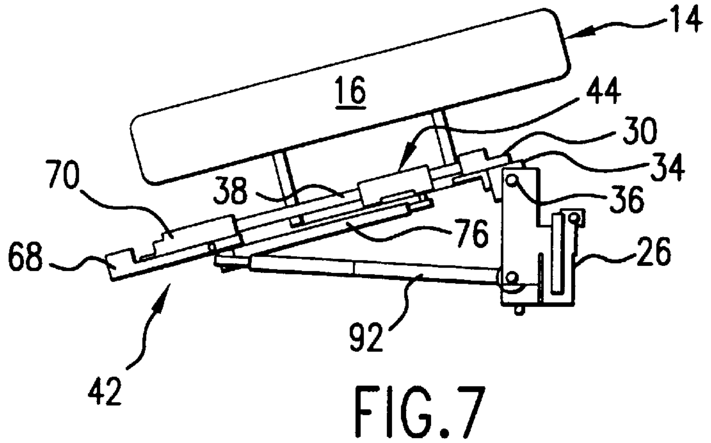
FIG. 7 is a side elevational view of the head section similar to FIG. 6 but showing the head section in tilt down position.

The operation of the head section 14 will now be described. When the practitioner desires to produce controlled flexion on a patient lying on the table with his or her head resting on the cushion 16 of the head section 14, the practitioner first determines the amount of tilt of the head section 14 depending upon the amount of flexion of the patient's cervical spine that is desired. The adjustment of the amount of flexion is made by loosening the locking nut 80 and positioning the lock block 78 in the desired position in slot 66 of the rocker arm 64. By moving the lock block 78 closer to the pivot of the rocker arm 64 provided by the roller bearing 74, the amount of downward tilt of the head section 14 will be decreased. On the other hand, by moving the lock block 78 farther from the pivot of the rocker arm 64 provided by the roller bearing 74, the amount of downward tilt of the head section 14 will be increased. By first pulling out the lock knob 94 to release the locking pin 97 from the locking member 96 and the then pressing down on the distal end of the head cushion 16, the push rod 92 will push the rocker arm 64 against the resistance of spring 90. Through the action of the linkage bar 76 which is joined to the slide bracket assembly 44, the slide bracket assembly 44 will move upwardly on the guide rods 38 causing the head section 14 to remain substantially in the same position relative to the chest-lumbar section 20 as the head section tilts. Thus, the gap between the head section 14 and chest-lumbar section 20 will not widen. As indicated above, the amount of head-flexion/tilt of the head section 14 can be adjusted by releasing the locking fastener 80 and then positioning the lock block 78 relative to the pivot 74 of the rocker arm 64. Regardless of the amount of tilt of the head section 14, the gap between the head section 14 and chest-lumbar section 20 will not change. This thus prevents excessive flexion to be induced upon the patient's cervical spine and will prevent any undesired traction on the patient's spine from occurring. The action of the linkage when the head section 14 is tilted downwardly is illustrated in FIG. 7.

Figure 6:
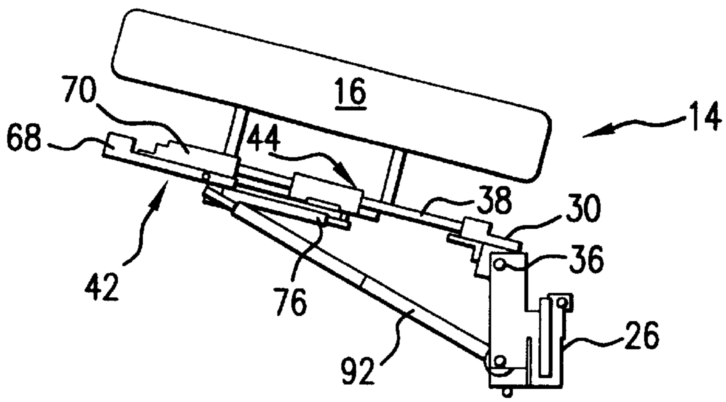
FIG. 6 is a side elevational view of the head section and illustrating the head section in a tilt up position.

If it is desired to tilt the head section 14 upwardly, this can also be done with the gap between the head section 14 and chest-lumbar section 20 being maintained. In other words, the cushion 16 on the head section 14 will not in any way interfere with the cushion on the chest-lumbar section 20. This action is illustrated in FIG. 6. When the head section 14 is tilted upwardly, the push rod 92 will pull on the rocker arm 64 which will pivot about the pivot point provided by fastener 72 thus causing the slide bracket assembly 44 to move outwardly on the guide rods 38 carrying with it the head section 14 which will be moved outwardly to maintain the gap between head section 14 and the chest-lumbar section 20.

The mechanism of the invention also provides for controlled traction of the patient's cervical spine if the practitioner so desires. By first unlocking the linkage bar 76 from the lock block 78 by loosening the lock bolt 84, the slide bracket assembly 44 is freed to slide on the guide rods 38. Because of the sliding action of the slide bracket assembly 44 along the guide rods 38, the practitioner can grasp the head section 14 and the patient's head and apply the desired traction. In other words, by releasing the lock bolt 84, the head section 14 is free to move inwardly and outwardly along the guide rods 38.

In all of the above actions, the return spring 90 will always return the head section 14 and cushion 16 to its normal position.

The mechanism of the invention can be used alone in the head section or it can be combined with any known structures. Thus, the mechanism of the invention does not interfere with known structures for producing rotation, lateral flexion or any drop or snap action. In other words, the mechanism of the invention can be used alone or combined with any known structures for producing one or more of the desired procedures.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is:

1. In a chiropractic treatment table having a supporting frame upon which rest multiple independent sections for supporting a patient and providing chiropractic adjustments of the patient's spine, the sections including a head section at one end of the table adjoining a second section that supports the patient's chest and lumbar spine, an improved head section providing head-flexion tilt comprising: a support block pivotally mounted to the supporting frame; a guide member attached to the support block and extending outwardly from the support block; a lock frame assembly combined with the guide member at a distal end of the guide member; a slide bracket assembly moveable generally in a horizontal plane along the guide member between the support block and the lock frame assembly; a patient support cushion combined with the slide bracket assembly and moveable therewith; the lock frame assembly including a rocker arm pivotally moveable about a pivot axis that is substantially perpendicular to the plane of movement of the slide bracket assembly, the rocker arm extending outwardly from the pivot axis generally transversely to the plane of movement of the slide bracket assembly and moveable about the pivot axis from a predetermined first position at rest to a second position when the head section is tilted; a linkage bar pivotally connected at one end to the rocker arm and pivotally connected at its other end to the slide bracket assembly; a push rod pivotally connected at one end to the supporting frame of the table and pivotally connected at its other end to the rocker arm opposite to the pivot connection of the rocker arm with the linkage bar; and a resilient member connected to the rocker arm and the support block biasing the rocker arm to its first position.

2. The improved head section of claim 1 in which the guide member is a pair of laterally spaced apart guide rods.

3. The improved head section of claim 1 in which the rocker arm has a slot extending outwardly from the pivot axis of the rocker arm and the end of the linkage bar connected to the rocker arm is movable along the slot, and a lock provides for locking the linkage bar in a selected position relative to the rocker arm.

4. The improved head section of claim 3 in which the lock frame assembly includes a releasable lock preventing pivotal movement of the rocker arm and thereby preventing tiltable movement of the head section.

5. The improved head section of claim 1 in which the linkage bar has a lock block at the end pivotally connected to the rocker arm, the linkage bar being slideable relative to the lock block, and a releasable locking fastener normally locks the linkage bar to the lock block, but provides for slideable movement of the slide bracket assembly along the guide member when the locking fastener is released.

* * * * *